(12) United States Patent
Rathbun et al.

(10) Patent No.: US 10,258,448 B2
(45) Date of Patent: Apr. 16, 2019

(54) IMPLANTABLE PROSTHESIS FOR SOFT TISSUE REPAIR

(71) Applicant: C.R. Bard, Inc., Murray Hill, NJ (US)

(72) Inventors: Tami L. Rathbun, Exeter, RI (US); Kathleen Corcoran, Brookline, MA (US); Marianne Staudenmeier, North Kingstown, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 713 days.

(21) Appl. No.: 14/387,073

(22) PCT Filed: Mar. 15, 2013

(86) PCT No.: PCT/US2013/032241
§ 371 (c)(1),
(2) Date: Sep. 22, 2014

(87) PCT Pub. No.: WO2013/142353
PCT Pub. Date: Sep. 26, 2013

(65) Prior Publication Data
US 2015/0088168 A1    Mar. 26, 2015

Related U.S. Application Data

(60) Provisional application No. 61/614,280, filed on Mar. 22, 2012.

(51) Int. Cl.
*A61F 2/00* (2006.01)
(52) U.S. Cl.
CPC .... *A61F 2/0063* (2013.01); *A61F 2210/0076* (2013.01)

(58) Field of Classification Search
CPC .. A61B 2017/0225; A61B 17/12022–17/1204;
(Continued)

(56) References Cited

U.S. PATENT DOCUMENTS 5,258,000 A    11/1993 Gianturco
5,634,931 A    6/1997 Kugel
(Continued)

FOREIGN PATENT DOCUMENTS

WO    WO 2016/105415 A1    6/2016

OTHER PUBLICATIONS

Extended European Search Report for European patent application No. 13765049.5, dated Nov. 23, 2015 (7 pages).
(Continued)

*Primary Examiner* — Ryan J. Severson
*Assistant Examiner* — Charles M Wei
(74) *Attorney, Agent, or Firm* — Wolf, Greenfield & Sacks, P.C.

(57) ABSTRACT

An implantable prosthesis for repairing or augmenting anatomical defects, including an inguinal hernia. The prosthesis may include a repair fabric having a body portion and a pocket on one side of the body portion to facilitate deployment and/or placement of the prosthesis at the defect site. For some applications, such as a reversible prosthesis, a second pocket may be provided on the opposite side of the body portion. Each pocket may be configured to receive a sufficient length of one or more fingers of an individual for deploying and/or positioning the prosthesis. A support member may be provided to help deploy the repair fabric at the surgical site and/or help inhibit folding or buckling of the repair fabric.

17 Claims, 4 Drawing Sheets

(58) Field of Classification Search
 CPC .................. A61B 17/12099–17/12122; A61B 17/12168–17/12177; A61B 2017/0212; A61F 2/0063–2002/0072; A61F 2/00–2/0009; A61F 2002/0068
 USPC ..................... 606/151–156; 623/23.72–23.74
 See application file for complete search history.

(56) References Cited

U.S. PATENT DOCUMENTS

| | | | | |
|---|---|---|---|---|
| 5,769,864 | A | * | 6/1998 | Kugel .................. A61F 2/0063 602/44 |
| 5,824,082 | A | * | 10/1998 | Brown .................. A61F 2/0063 623/11.11 |
| 5,922,026 | A | * | 7/1999 | Chin .................. A61B 17/0057 606/151 |
| 6,224,616 | B1 | * | 5/2001 | Kugel .................. A61F 2/0063 128/898 |
| 6,551,356 | B2 | | 4/2003 | Rousseau |
| 6,790,213 | B2 | | 9/2004 | Cherok et al. |
| 7,101,381 | B2 | | 9/2006 | Ford et al. |
| 8,945,235 | B2 | | 2/2015 | Horton et al. |
| 9,005,223 | B2 | | 4/2015 | Cardinale et al. |
| 9,072,586 | B2 | | 7/2015 | Ranucci et al. |
| 2004/0215219 | A1 | * | 10/2004 | Eldridge ................ A61F 2/0063 606/151 |
| 2006/0064175 | A1 | * | 3/2006 | Pelissier ................ A61F 2/0063 623/23.72 |
| 2006/0253203 | A1 | | 11/2006 | Alvarado |
| 2007/0299538 | A1 | | 12/2007 | Roeber |
| 2010/0286716 | A1 | * | 11/2010 | Ford .................. A61B 17/0057 606/151 |
| 2011/0152993 | A1 | * | 6/2011 | Marchand ........ A61B 17/12022 623/1.2 |
| 2013/0103058 | A1 | | 4/2013 | Gobran |
| 2014/0316444 | A1 | | 10/2014 | Pankratz |
| 2015/0080918 | A1 | | 3/2015 | Lecuivre et al. |
| 2015/0094743 | A1 | | 4/2015 | Russo et al. |
| 2016/0151139 | A1 | | 6/2016 | Pankratz et al. |
| 2016/0374790 | A1 | | 12/2016 | Jacinto |

OTHER PUBLICATIONS

International Search Report and Written Opinion for PCT/US13/32241, dated Jun. 10, 2013 (12 pages).
International Preliminary Report on Patentability for PCT/US13/32241, dated Sep. 23, 2014 (9 pages).

* cited by examiner

IMPLANTABLE PROSTHESIS FOR SOFT TISSUE REPAIR

BACKGROUND OF INVENTION

1. Field of Invention

The present invention relates to an implantable prosthesis, and more particularly, to a prosthesis for repairing or augmenting defects and/or weaknesses in a soft tissue or muscle wall.

2. Discussion of Related Art

Various prosthetic repair materials are known for repairing and reinforcing anatomical defects, such as soft tissue and muscle wall hernias. For example, ventral and inguinal hernias are commonly repaired using a sheet of biocompatible fabric, such as a knitted polypropylene mesh (e.g., BARD MESH). Once inserted into a patient, the fabric is typically sutured, stapled, tacked or otherwise provisionally anchored in place over, under or within the defect. Tissue integration with the fabric, such as by tissue ingrowth into the fabric, eventually completes the repair.

It is an object of the present invention to provide a method and prosthesis for repairing and/or reinforcing soft tissue and muscle walls.

SUMMARY

The present invention relates to an implantable prosthesis for repairing an anatomical defect, such as a tissue or muscle wall hernia, including an inguinal hernia.

In one embodiment, an implantable prosthesis is provided for repairing a tissue or muscle wall defect. The implantable prosthesis comprises a patch of repair fabric including a body portion that is constructed and arranged to cover the tissue or muscle wall defect, and first and second pockets to facilitate deployment and/or placement of the prosthesis at the tissue or muscle wall defect. The first pocket is located on a first side of the body portion and the second pocket is located on a second side of the body portion opposite the first side.

In another embodiment, an implantable prosthesis is provided for repairing a tissue or muscle wall defect. The implantable prosthesis comprises a patch of repair fabric including a body portion that is constructed and arranged to cover the tissue or muscle wall defect, and at least one pocket to facilitate deployment and/or placement of the prosthesis at the tissue or muscle wall defect. The patch has an oval shape with a major axis and a minor axis. The patch includes an obtuse end portion and an acute end portion with the obtuse end portion being larger than the acute end portion. The at least one pocket is located at the obtuse end portion of the patch.

Various embodiments of the present invention may provide certain advantages and may overcome certain drawbacks of prior prostheses. Embodiments of the invention may not share the same advantages, and those that do may not share them under all circumstances.

BRIEF DESCRIPTION OF DRAWINGS

Various embodiments of the invention will now be described, by way of example, with reference to the accompanying drawings, in which.

DESCRIPTION

Figure 1:
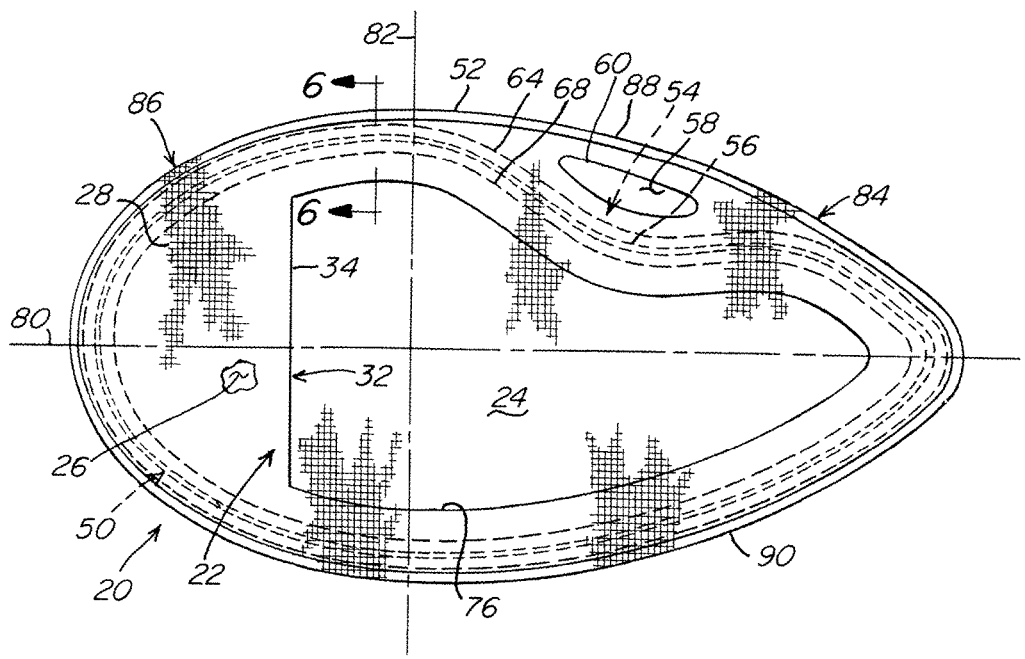
FIG. 1 is a plan view of an implantable prosthesis for soft tissue repair according to one illustrative embodiment.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments discussed herein may be implemented in any of numerous ways, as the disclosed concepts and embodiments are not limited to any particular manner of implementation. In addition, it should be understood that aspects of the invention may be used alone or in any suitable combination with other aspects of the invention.

The invention is directed to an implantable prosthesis for repairing or augmenting anatomical defects, and is particularly suitable for the repair of defects in, and weaknesses of, soft tissue and muscle walls or other anatomical regions. The prosthesis may promote tissue or muscle ingrowth thereto and subsequently strengthen the area of the defect. The prosthesis may be configured to provide a surgeon an ability to readily deploy and/or manipulate the prosthesis into position.

For ease of understanding, and without limiting the scope of the invention, the prosthesis is described below particularly in connection with the repair of an inguinal hernia. It should be understood, however, that the prosthesis is not so limited and may be employed in other anatomical procedures, as should be apparent to one of skill in the art. For example, and without limitation, the prosthesis may be employed for ventral hernias, chest or abdominal wall reconstruction, or large defects, such as those that may occur in obese patients. The prosthesis may include one or more features, each independently or in combination, contributing to such attributes.

The invention is more particularly directed to a prosthesis that includes a repair fabric having a body portion that is configured to cover or extend across the defect opening or weakness when the body portion is placed against the defect. The prosthesis may be in the form of a patch, although the prosthesis may employ other configurations as should be apparent to one of skill in the art.

The prosthesis includes at least one pocket located on one side of the body portion to facilitate deployment and/or placement of the repair fabric. The pocket may be configured to receive a sufficient length of one or more fingers of an individual's hand (or a suitable surgical instrument) for deploying and/or placing the prosthesis. The pocket may be located at an end portion of the prosthesis. However, the pocket may employ any suitable configuration and/or may be located at any suitable portion of the prosthesis as should be apparent to one of skill in the art.

The pocket may be created with a layer of fabric that is attached to the body portion in a manner that forms the pocket therebetween. An opening may be provided for permitting access of an individual's fingers (or surgical instrument) therethrough and into the pocket. The opening may be located along an edge of the layer of fabric. Alternatively, the opening may be formed through the layer of fabric creating the pocket.

For some applications, it may be desirable to employ a prosthesis that is reversible, such as for both left hand and right hand applications, in which the prosthesis may be flipped or turned over depending on the application. For such applications, the prosthesis may include pockets located on opposite sides of the body portion so that a pocket is available for deploying and/or positioning the prosthesis regardless of its orientation for the particular application. The pockets may be located on opposite sides of the same portion, such as end portions, of the prosthesis or at different portions of the prosthesis.

The prosthesis may have a non-circular shape, such as a generally oval, elliptical or egg shape, that is suitable for augmenting or repairing an inguinal hernia. The prosthesis may be configured with a generally oval shape (e.g., egg shape) having a narrower or acute end portion and a wider or obtuse end portion. Each pocket may be provided at the obtuse end portion of the prosthesis, although other pocket arrangements are contemplated as should be apparent to one of skill in the art.

If desired, any pocket that will not to be employed during the repair procedure may be removed by the user prior to insertion of the prosthesis into the patient to reduce the amount of material being implanted into the patient. For example, and without limitation, the layer of material forming an unused pocket may be trimmed or cut away from the prosthesis.

The repair fabric and pocket forming layers may be formed of a tissue infiltratable material, such as a knit fabric, or may be composed of a solid or substantially non-porous material. The repair fabric may be formed of one or more layers of the same or dissimilar material. The repair fabric and/or pocket layers may be formed with portions that are tissue infiltratable and other portions that are non-tissue infiltratable, providing selected areas of the repair device with different tissue ingrowth and adhesion resistant properties. The repair fabric and/or pocket layers may be formed of non-absorbable material, absorbable material or a combination of absorbable and non-absorbable materials.

The prosthesis may include a member, such as a support or stiffening member, or a support assembly that is attached to or integrated with the repair fabric to facilitate manipulation and deployment of the prosthesis at the surgical site and/or help inhibit folding or buckling of the repair fabric. The support member or support assembly may completely surround or substantially surround the body portion, such as in a ring-like manner, to help deploy and/or hold the body portion in an open or spread out configuration for covering the defect. The support member may have a resiliency or other property that allows the support member to deform from an initial shape and then return to the initial shape to return the body portion to the spread out configuration. For example, and without limitation, the support member may be rollable, foldable or otherwise collapsible, when the repair fabric is reduced in size for delivery to the repair site, and may spring back, either automatically or upon the influence of a force (e.g., body heat where the support is formed of a shape memory material, such as NITINOL) to its initial expanded shape on deployment at the repair site, influencing the prosthesis to assume its unfurled or spread out configuration.

The support member may be formed of a monofilament that has been preformed into the desired shape or may be placed into the desired shape during assembly of the prosthesis. The support member may be comprised of a non-absorbable or an absorbable material.

A support assembly may include a support or stiffening member that is surrounded by material that separates the member from the layer of material. The support member may be located in a sleeve of material, such as a tube of fabric. The sleeve may include interstices or openings that allow tissue or muscle ingrowth and/or facilitate absorption of an absorbable support member.

The prosthesis may be placed at the defect site using an open surgical procedure, or by laparoscopically passing the device through a cannula to the defect. The repair fabric may be flexible, allowing reduction of the prosthesis, such as by folding, rolling or otherwise collapsing the repair fabric, into a slender configuration suitable for delivery to the defect site. Upon delivery, the repair fabric may automatically open to an unfurled or spread out configuration, or may be unfolded, unrolled or otherwise deployed by the surgeon to an unfurled or spread out configuration suitable to repair the weakness or defect. The surgeon may insert one or more fingers (or surgical instrument) into a pocket to deploy and/or place the prosthesis in the desired position at the defect site.

Figure 2:
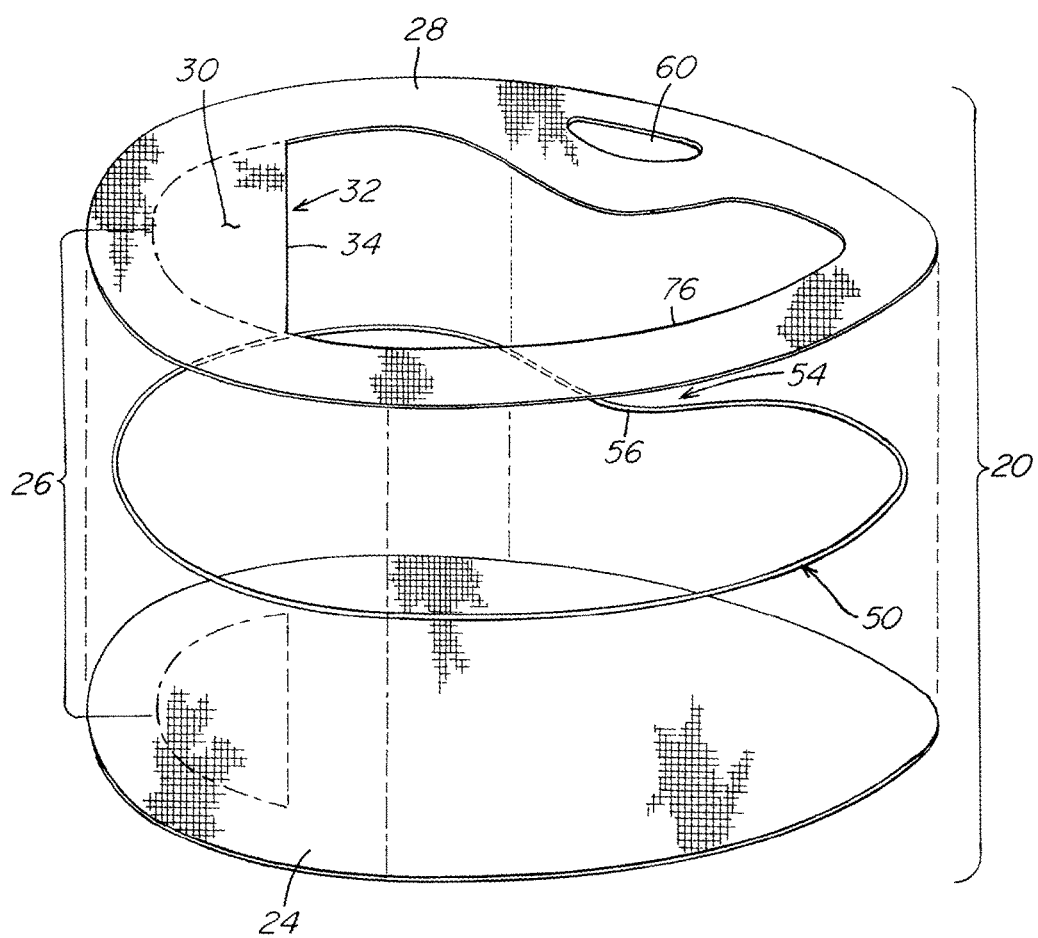
FIG. 2 is an exploded perspective view of the implantable prosthesis of FIG. 1.

FIGS. 1-2 illustrate one embodiment of an implantable prosthesis 20 for repairing or augmenting soft tissue and muscle wall defects, such as an inguinal hernia. The prosthesis 20 includes a repair fabric of implantable, biologically compatible material with a body portion 22 that is configured to cover or extend across a defect. As shown, the prosthesis is configured as a patch that may be used as an underlay or an overlay. The prosthesis may be configured with any desired strength, flexibility, tissue integration, adhesion resistance and/or other characteristics suitable for the repair as should be apparent to one of skill. Although the prosthesis is described in connection with a patch-type embodiment, the prosthesis may include a plug, a combination plug and patch, and other suitable arrangements for mending the defect.

The repair fabric includes at least one layer of tissue infiltratable material that permits or is otherwise susceptible to tissue ingrowth. In one embodiment, the repair fabric includes a first layer 24 of a biologically compatible, flexible material that includes a plurality of interstices or openings which allow sufficient tissue or muscle ingrowth to secure the prosthesis to host tissue or muscle after implantation.

To facilitate deployment and/or placement of the prosthesis at the defect site, the prosthesis may include at least one pocket 26 located on one side of the body portion. In this manner, a surgeon may use the pocket to locate the prosthesis in the desired position at the defect site. In one embodiment, the pocket 26 may be configured to receive a length of one or more fingers that extends from the fingertip to a portion of the finger extending from about the first knuckle to about the second knuckle, although other suitably sized pockets may be employed, as the present invention is not limited in this respect.

In one embodiment, a first pocket 26 is created by attaching a second layer 28 of material to the first layer 24 in a manner to form the pocket therebetween. As shown, a portion 30 of the second layer 28 extends across a portion of the first layer 24 to create the pocket. The layers of fabric may be attached using any suitable technique as should be apparent to one of skill in the art. For example, and without limitation, the layers may be attached together with one or more stitch lines; the layers may be bonded together by melting the layers at specific locations or in a specified pattern; sonic, induction, vibration or infrared/laser welding the layers; or using a suitable bonding agent.

To gain access to the interior of the pocket, an opening 32 may be provided for receiving an individual's fingers or an instrument therethrough and into the pocket. The opening 32 may be located along an edge 34 of the second layer 28 of fabric. For example, and without limitation, an unattached length or segment of an edge of the second layer extends across a portion of the body portion to form the opening to the pocket. If desired, the opening may be formed through the layer of fabric creating the pocket. However, it is to be appreciated that the prosthesis may include any suitable opening that allows access to the pocket as should be apparent to one of skill in the art.

As illustrated, the pocket 26 may be located at an end portion of the prosthesis. However, it is to be appreciated that the pocket may be located on any portion of the prosthesis suitable for deploying and/or positioning the prosthesis as should be apparent to one of skill in the art.

For some applications, it may be desirable to employ a prosthesis that is reversible, such as for both left hand and right hand applications, in which the prosthesis is turned over from one side to the opposite side depending on the repair procedure. For such applications, the prosthesis may include pockets located on opposite sides of the body portion so that a pocket is available for deploying and/or positioning the prosthesis regardless of its orientation for the particular application. The pockets may be located on opposite sides of the same end portion of the prosthesis or at opposite end portions of the prosthesis.

Figure 3:
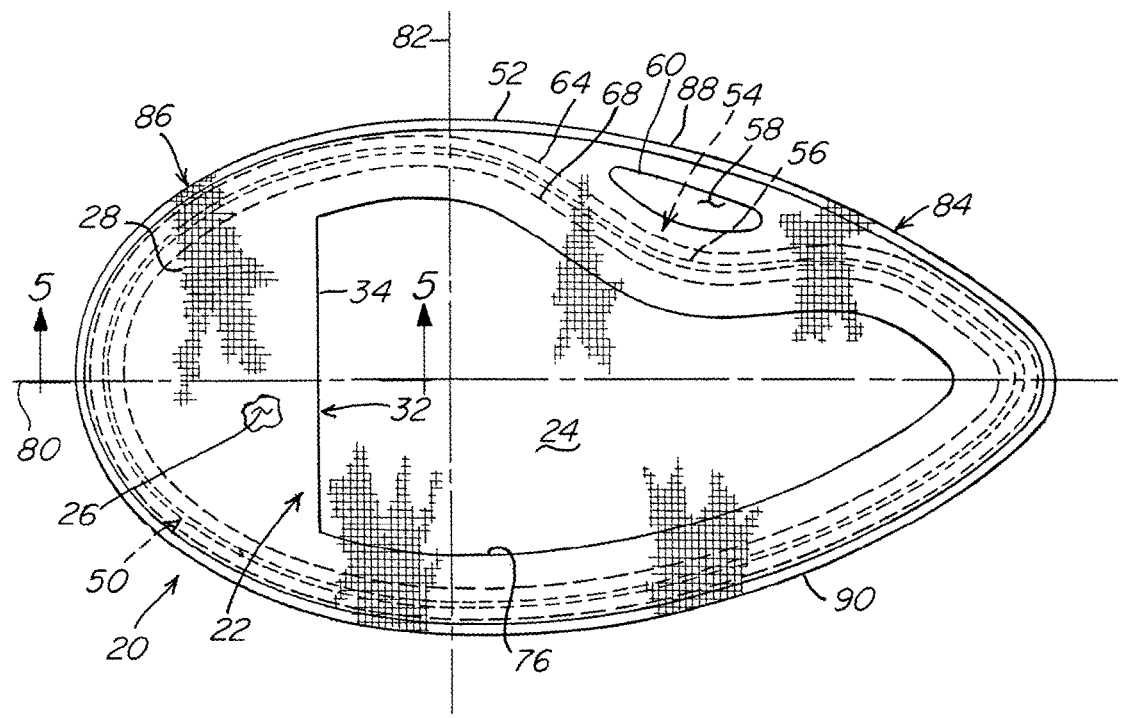
FIG. 3 is a plan view of an implantable prosthesis for soft tissue repair according to another illustrative embodiment.
Figure 5:
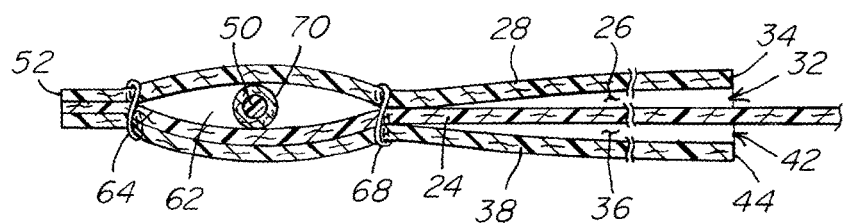
FIG. 5 is a cross sectional view taken along section line 5-5 of FIG. 3.
Figure 4:
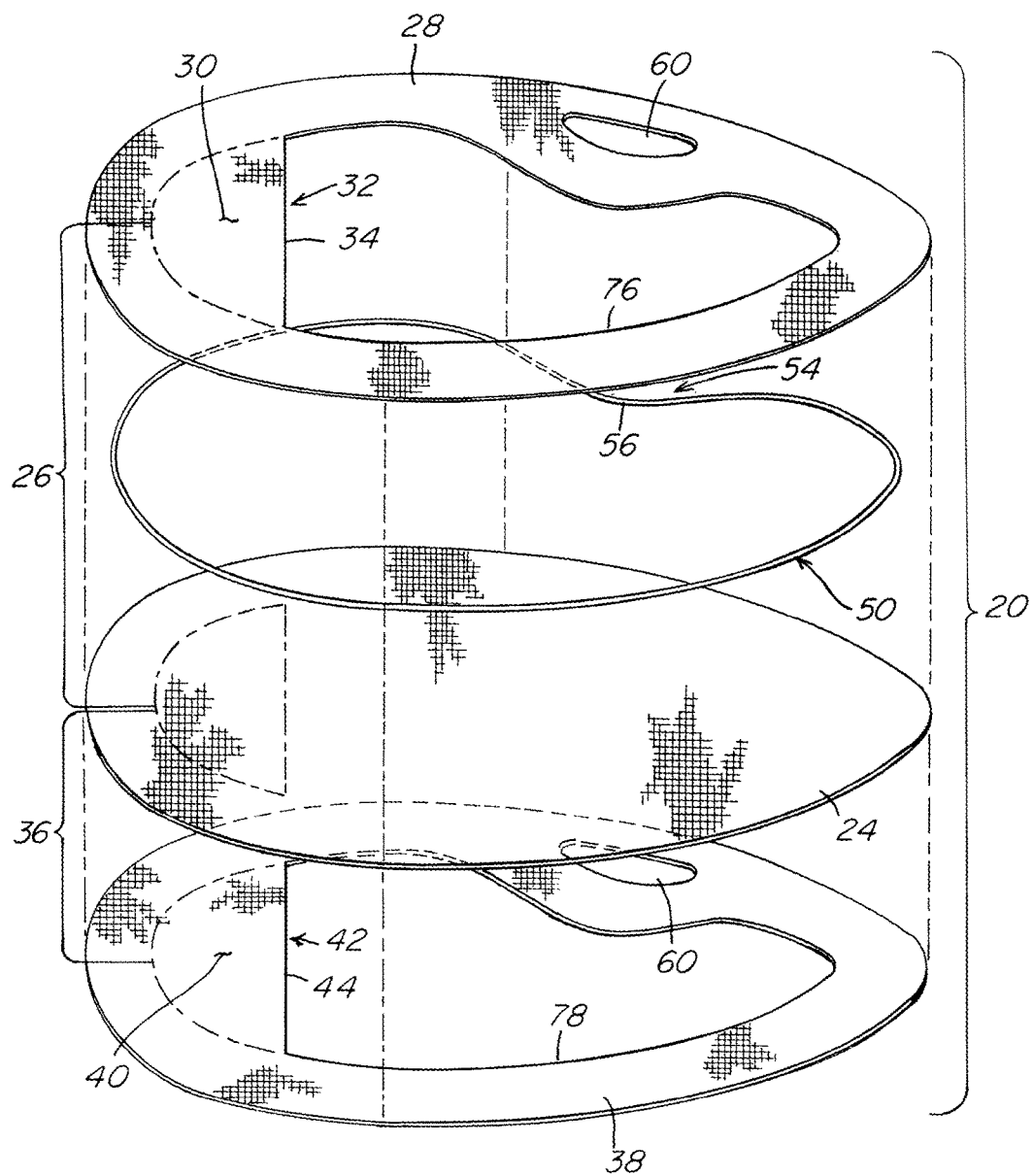
FIG. 4 is an exploded perspective view of the implantable prosthesis of FIG. 3.

In one illustrative embodiment shown in FIGS. 3-5, a second pocket 36 is created by attaching a third layer 38 of material to the first layer 24 in a manner to form the second pocket therebetween. As shown, a portion 40 of the third layer 38 is configured to extend across a portion of the second surface of the first layer 24 to create the pocket. The layers of fabric may be attached using any suitable technique, such as those described above, as should be apparent to one of skill in the art.

An opening 42 may be provided to gain access to the second pocket. Similar to the first pocket, the opening 42 may be located along an edge 44 of the third layer in a manner as described above.

If desired, any pocket that is not to be employed during the repair procedure may be removed by the user prior to insertion into the patient to reduce the amount of material being implanted into the patient. For example, and without limitation, the layer of material forming an unused pocket may be trimmed or cut away from the prosthesis. The layer of fabric creating a pocket may be formed of an absorbable or non-absorbable material or a combination of absorbable and non-absorbable materials as should be apparent to one of skill in the art.

To help deploy the patch into a spread out configuration for covering a defect or weakness, it may be desirable to employ a patch that is sufficiently rigid so that it can be easily and effectively manipulated and positioned in the desired area, yet sufficiently flexible so that the patch may be adequately handled by the physician implanting the patch and tolerated by the patient receiving the patch.

In one illustrative embodiment as shown in FIGS. 1-4, to balance the stiffness and flexibility characteristics, the prosthesis 20 may include a support member 50 to reinforce portions of the patch and to help deploy and/or hold the patch in a spread out configuration. The support member 50 may be coupled to the patch in any suitable manner, as the present invention is not limited in this respect. Suitable attachment methods include, but are not limited to, stitching, bonding, adhesive, and integral formation with the repair fabric of the patch, as will be discussed further below.

The support member 50 contributes to the stability of the patch, allowing it to deploy into and remain in a desired shape. For example, the support member may aid in returning the patch to a substantially unfurled or spread out configuration after the folded up or otherwise reduced prosthesis has been delivered to the repair site through either an open incision or a cannula. This stability facilitates deployment and placement of the patch by making it easy to handle. Also, this stability minimizes the tendency of the patch to fold, bend, or otherwise be dislocated. Difficulty in handling, dislocation or bending could require additional operative procedures and/or additional anchoring during implantation.

In one embodiment, the support member includes a continuous loop or ring positioned adjacent the outer margin of the patch. In the illustrative embodiment, the support member 50 is spaced inwardly from the outer peripheral edge 52 of the repair fabric. However, it should be appreciated that the present invention is not limited in this respect, as the support member 50 may be disposed at the peripheral edge and/or at discrete locations throughout the body of the patch.

As shown, the support member 50 may be configured to completely surround the body portion so as to help deploy and/or hold the body portion 22 in the spread out configuration for covering the defect. Alternatively, the support member may include one or more interruptions formed by spacing ends of the member apart. An interruption may be located at any suitable region of the prosthesis as should be apparent to one of skill in the art.

In certain repair procedures, it may be desirable to configure the support member so as to accommodate a particular body structure at the repair site. In one embodiment, the support member may be configured to avoid the femoral vessels or cord structures during an inguinal hernia repair.

In one illustrative embodiment shown in FIGS. 1-4, the support member 50 may include an indentation or notch 54 that is configured to accommodate the particular body structure. As shown, a portion 56 of the support member 50 may deviate inwardly away from the outer periphery 52 of the patch to form the indentation. The overall support member 50 may have a generally convex curvature as it extends about the body portion 22 while the portion 56 of the support member forming the indentation 54 may have a generally concave curvature. In this manner, the indentation 54 may have a curved shape that extends about the body structure when the prosthesis is implanted at the defect site.

In the illustrative embodiments shown in FIGS. 1 and 3, a segment 58 of repair fabric may occupy the region of the patch at the indentation 54 between the support member 50 and the outer periphery 52. In some instances, a surgeon may wish to retain this segment 58 of repair fabric on the prosthesis for the repair procedure. For example, a surgeon may find it desirable to enhance tissue ingrowth in the vicinity of the femoral vessels in an inguinal hernia repair. In other instances, a surgeon may find it desirable to remove this segment of the repair fabric from the prosthesis.

As illustrated, one or both of the second and third layers of material may include a cutout 60 in the region of the indentation to reduce the amount of material that is implanted in a patient. Alternatively, the prosthesis 20 may be constructed so that the outer periphery 52 of the patch follows the contour of the support member 50 at the indentation 54 so that excess fabric material would not need to be removed by the surgeon.

In the illustrative embodiments shown in FIGS. 1-4, the support member 50 includes a single indentation 54 for accommodating a body structure during a repair procedure. However, it is to be appreciated that two or more indentations may be provided so as to accommodate multiple structures in the repair site. Additionally, the support member may include a pair of indentations that are symmetrically positioned on the patch so that the prosthesis may be readily employed for various repairs, such as left and right side inguinal hernia repairs. However, it is to be understood that multiple indentations are not required to employ the prosthesis for repairing both left side and right side inguinal hernias. As one of ordinary skill in the art should appreciate, a prosthesis with a single indentation 54, such as the prosthesis 20 shown in FIGS. 1-4, may be employed for both left side and right side inguinal hernia repairs by turning over the prosthesis.

The support member 50 may be disposed on the patch in any suitable manner as the present invention is not limited in this respect. In one embodiment, as shown in FIGS. 2 and 4-6, the support member 50 is sandwiched between the first and second layers 24, 28 of material and may or may not be physically attached thereto. The support member 50 may be tightly or loosely held within a channel 62 between the first and second layers and formed by a pair of seams 64, 68 joining the first and second layers. In the illustrative embodiment, the channel 62 is formed by a pair of seams that follow the contour of the support member 50. The seams may be formed by a series of stitches extending along the outside and inside edge of the support member 50 to keep it from moving with respect to the first and second layers 24, 28. Because of the rigidity of the support member 50, one seam extending along one side of the support member may be sufficient.

It should be appreciated that the invention is not limited to any particular attachment method, as the first and second layers 24, 28 may be attached along the seams 64, 68 or other desired locations using other suitable techniques. For example, the layers may be bonded together by melting the layers at specific locations or in a specific pattern; sonic, induction, vibration, or infrared/laser welding the layers; or using a suitable bonding agent. The point or points of attachment may comprise any suitable pattern as should be apparent to one of skill in the art.

Alternatively, rather than being sandwiched between the first and second layers, the support member 50 may overlie or underlie the repair fabric and may be attached, regardless of location, with stitches or a bonding agent, or fused with ultrasonic, induction, vibration, infrared/laser welding and the like. Alternatively, the support member 24 may be woven through at least one of the layers or integrally formed with one or both layers during fabrication of the layer itself.

Figure 6:
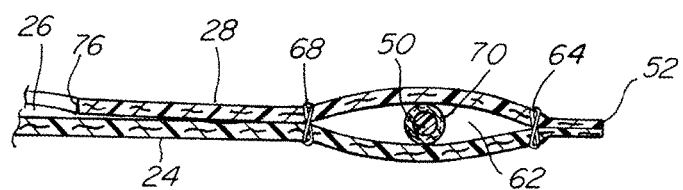
FIG. 6 is a cross sectional view taken along section line 6-6 of FIG. 1.

In one illustrative embodiment shown in FIGS. 5 and 6, the support or stiffening member 50 may be surrounded with material that separates the support member from the first and second layers 24, 28. In one embodiment, the stiffening member 50 may be located in a sleeve of material 70. However, it is to be understood that the support assembly may employ other suitable arrangements apparent to one of skill in the art to surround the support member with material that separates the support member 50 from the first and second layers.

In one illustrative embodiment shown in FIGS. 1-4, the first layer 24 may be configured as a full layer of fabric material that is sized and shaped to cover the defect. The second and third layers 28, 38 have a generally annular configuration that overlies and generally follows the contour of the support member to reduce the overall amount of material for the prosthesis. As described above, an end portion 30, 40 of the second and third layers 28, 38 is configured to extend across and cover a corresponding portion of the first layer to form the first and second pockets. As shown, the second and third layers may have an inner edge 76, 78 that is configured to follow the contour of the support member other than at the end portions of the layers forming the pocket.

The prosthesis may be configured to have any suitable shape or size that is conducive to facilitating the correction or repair of a particular defect, such as an inguinal hernia. In the embodiments shown in FIGS. 1-4, the patch has a relatively flat configuration. However, the patch need not be flat, and convex, concave, convex/concave, and more complex three-dimensional shapes also are contemplated. The patch may be pliable to facilitate manipulation and/or reduction of the patch during delivery to the defect and/or to conform the patch to the anatomical site of interest.

In the illustrative embodiments shown in FIGS. 1-4, the prosthesis has a generally oval, elliptical or egg shape suitable for augmenting or repairing an inguinal hernia in the inguinal canal. The geometry of the prosthesis 20 is generally oval with a major axis 80 extending along the longest portion of the prosthesis and a minor axis 82 extending across the widest portion of the prosthesis in a direction perpendicular to the major axis. As illustrated in FIGS. 1 and 3, the outer periphery 52 of the prosthesis is substantially symmetric about the major axis 80 and is substantially asymmetric about the minor axis 82, providing a generally oval shape (e.g., egg shape) with a narrower or acute end 84, a wider or obtuse end 86, and opposing sides 88, 90 that converge towards each other in a direction from the obtuse end 86 toward the acute end 88. It is to be appreciated that the prosthesis may be configured with any suitable shape, such as a shape that is symmetric about both axes, asymmetric about both axes, or asymmetric about the major axis and symmetric about the minor axis. Examples of other shapes include, but are not limited to, circular, square, rectangular, and irregular configurations. The repair fabric may be sized to cover part or, preferably, all of the defect.

The obtuse end 86 has a rounded configuration that generally conforms to the shape of the repair site, such as the medial corner of the inguinal canal. The obtuse end 86 is configured to overlie and cover the defect. The acute end 84 of the prosthesis is configured to generally be positioned at the repair site away from the defect. Therefore, the acute end may have a smaller configuration relative to the obtuse end to reduce the overall amount of material introduced by the prosthesis during a repair procedure. As shown, the acute end portion may have a relatively narrow configuration as compared to an obtuse end portion with a relatively wide configuration. However, it is to be understood that the obtuse end and the acute end may have any suitable configurations apparent to one of skill in the art.

The pockets 26, 36 and pocket openings 32, 42 may be positioned in any desirable location, relative to the body portion 22, that is suitable for a particular repair. In the illustrative embodiments, the pockets are located at the obtuse end portion of the patch with the openings located away from the minor axis 82 toward the obtuse end portion 86 of the prosthesis. However, it is to be appreciated that the prosthesis is not so limited and the locations of the pockets and/or openings may be varied for other repairs as should be apparent to one of skill in the art.

The indentation 54 may be positioned in any desirable location, relative to the body portion 22, that is suitable for a particular repair. In the illustrative embodiment, the indentation 54 is positioned offset from the minor axis 82 toward the acute end 84 of the prosthesis. As shown, the indentation 54 may be located entirely to one side of the minor axis toward the acute end. The illustrated embodiment of the indentation is particularly suited for repair of an inguinal hernia. However, it is to be appreciated that the prosthesis is not so limited and the location of the indentation may be varied for other repairs as should be apparent to one of skill in the art.

As indicated above, the prosthesis 20 may be used in the repair of an inguinal hernia. More particularly, the prosthesis illustrated in FIGS. 1-4 is particularly suited for a direct inguinal hernia. The obtuse end of the body portion 22 is configured to be placed over the hernia defect and the indentation 54 is configured to be positioned adjacent the femoral vessels or cord structures. As indicated above, the segment 58 of repair fabric (FIG. 1) may be retained for the repair or removed as desired by a surgeon.

The repair fabric may include at least one layer of tissue infiltratable material that permits or is otherwise susceptible to tissue or muscle ingrowth to enhance the repair of the defect. In one embodiment, each of the layers 24, 28, 38 is formed of a biologically compatible, flexible repair material that includes a plurality of interstices or openings which allow sufficient tissue or muscle ingrowth to integrate the prosthesis with host tissue or muscle after implantation. Multiple layers of tissue infiltratable fabric may enhance the strength of the patch and/or the amount of tissue ingrowth to the patch. Preferably, the first and second layers are formed of the same tissue infiltratable material. However, the invention is not limited in this respect, and any one or each layer may be formed of any biologically compatible material, suitable for repairing a tissue or muscle wall defect as should be apparent to one of skill.

In one embodiment, the first, second and third layers 24, 28, 38 of the prosthesis 20 are each formed from a sheet of knitted mesh fabric. When implanted, the polypropylene mesh promotes rapid tissue or muscle ingrowth into and around the mesh structure. Examples of surgical materials which may be utilized for the layers and are suitable for tissue or muscle reinforcement and defect correction include BARD MESH (available from C.R. Bard, Inc.), BARD SOFT MESH (available from C.R. Bard, Inc.), SOFT TISSUE PATCH (microporous ePTFE—available from W.L. Gore & Associates, Inc.); SURGIPRO (available from US Surgical, Inc.); TRELEX (available from Meadox Medical); PROLENE and MERSILENE (available from Ethicon, Inc.); and other mesh materials (e.g., available from Atrium Medical Corporation). Absorbable or resorbable materials, including polyglactin (VICRYL—available from Ethicon, Inc.) and polyglycolic acid (DEXON—available from US Surgical, Inc.), may be suitable for applications involving temporary correction of tissue or muscle defects. Collagen materials such as COOK SURGISIS, available from Cook Biomedical, Inc. may also be used. It also is contemplated that the mesh fabric may be formed from multifilament yarns and that any suitable method, such as knitting, weaving, braiding, molding and the like, may be employed to form the mesh material.

In the embodiments shown, the support member 50 includes a monofilament of a desired thickness and cross-sectional shape to provide a desired degree of resilience or rigidity. It should be appreciated that the support member may have any cross-sectional shape, such as circular, square, rectangular, triangular, elliptical, etc. The support member may be configured on the patch in any pattern, such as a spiral pattern, a square pattern, an elliptical pattern, a circular pattern, crisscross pattern or the like.

In one embodiment, the support member 50 is formed of an absorbable material. The absorbable support member facilitates initial handling and deployment of the prosthesis. Thereafter, the support member will gradually degrade until it is completely absorbed by the body. Such an arrangement may be advantageous in that the support member is eventually absorbed by the body after it is no longer needed to facilitate the handling and deployment of the prosthesis.

In one embodiment, the support member 50 is formed from a polydioxonane (PDO) monofilament that may have a diameter of approximately 0.038 inches. However, it is contemplated that the support member may be formed of any biocompatible, absorbable or non-absorbable material, including monofilaments, multifilaments or molded shapes, provided suitable stiffness and handling properties are maintained. It should be appreciated that the support member (or the individual filaments or bands collectively forming the support member) may have any suitable cross-sectional size and shape, such as circular, square, rectangular, triangular, elliptical, etc.

The sleeve 70 may be formed of a porous material that allows passage or infiltration of fluid and/or tissue to promote degradation and/or absorption of the support member 50. In one embodiment, the material includes interstices or pores having a size from approximately 0.00035 in$^2$ to approximately 0.00085 in$^2$. It may be desirable to employ a sleeve having an interstice or pore size of approximately 0.00085 in$^2$ when the support assembly is used with an ingrowth layer 22 formed of material having a similar pore or interstice size of approximately 0.00085 in$^2$. A sleeve having a smaller interstice or pore size, such as approximately 0.00035 in$^2$, may be desired when the support assembly is used with an ingrowth layer 22 formed of material having a larger pore or interstice size, such as greater than 0.00085 in$^2$. However, it is to be understood that the sleeve may employ material having other suitable interstice or pore sizes as would be apparent to one of skill in the art.

In one embodiment, the sleeve 70 is formed from a mesh fabric that includes interstices or pores that allow tissue infiltration or ingrowth into the support assembly to eventually surround and absorb the support member 50. In one embodiment, the sleeve is formed from a knitted polypropylene mesh. The mesh may be knitted with monofilament having a diameter of approximately 0.006 inches. The mesh may employ any suitable fabric pattern that provides desired properties. It is to be understood that the sleeve may be formed of any suitable mesh material including, but not limited to, the material used for the ingrowth layer or other biocompatible materials having suitable properties. It also is contemplated that the sleeve may be formed from multifilament yarns and that any suitable method, such as knitting, weaving, braiding, molding and the like, may be employed to form the sleeve.

In one illustrative embodiment, the sleeve may be configured as a unitary member that is formed with a single piece of material. In one illustrative embodiment shown in FIGS. 5-6, the support assembly may employ a sleeve 70 configured as a tubular or sock-like member that receives the support member 50 therein. In one embodiment, the sleeve is a tubular mesh fabric material. Alternatively, the sleeve may be formed with two rings of mesh that are attached to form the sleeve. In this alternate arrangement, the support member may be sandwiched between the mesh rings which are attached to each along the inner and outer sides of the support member to surround the support member in a sleeve of material. A suitable support assembly is described in more detail in U.S. application Ser. No. 13/122,257, assigned to C.R. Bard, which is incorporated herein by reference.

Although several illustrative embodiments have been provided for the support assembly, it is to be understood that the support assembly may employ other structural arrangements as should be apparent to one of skill in the art.

Although the support member 50 is described as being formed of a monofilament, other suitable constructions may be employed. For example, the support member may be molded elements that are subsequently attached to the patch or molded onto the patch. As another example, the support member may be formed from the repair fabric. In this respect, the support member may be formed by melting a portion of the repair fabric in any desired shape. In another example, the support member may be formed by multiple stitches passing through one or more layers, such as, for example, an embroidered section. Alternatively, the support member may be formed by altering the weave pattern in a zone of desired reinforcement. In this manner, the area of the repair fabric where tissue ingrowth may be desired may be formed with a relatively loose open weave, whereas the area or zone of reinforcement may be formed with a relatively tight weave, to provide the desired rigidity. Other suitable methods or mechanisms to form the support member may be employed, as the present invention is not limited in this respect.

For some applications, the prosthesis may include an adhesion resistant barrier overlying at least a portion, and preferably all, of one side of the repair fabric and/or pocket layers and/or an edge barrier to isolate one or more edges of the patch from adjacent tissue, muscle or organs. The barrier layer and/or edge barrier may be formed of a material and/or with a structure that does not substantially stimulate and, in certain embodiments, may resist tissue, muscle or organ ingrowth and adhesion formation when implanted, thereby reducing the incidence of undesired postoperative adhesions between the ingrowth layer and adjacent tissue, muscle or organs. If desired, such a barrier layer and/or edge barrier may be formed from any suitable material or structure as should be apparent to one of skill in the art, including, but not limited to, a sheet of expanded polytetrafluoroethylene (ePTFE) having a microporous pore structure that inhibits tissue ingrowth. Alternatively, a barrier layer may be formed of an absorbable material as should be apparent to one of skill in the art.

The illustrative embodiments of the prosthesis may be particularly suited for inguinal hernia repair. In one embodiment, it is contemplated that the prosthesis may be placed in the pre-peritoneal space via an open repair to strengthen the myopectineal orifice. The defect may be repaired using an anterior approach (similar to a mesh plug technique) or a posterior approach (similar to the known Kugel technique). Deployment and proper placement of the prosthesis in the pre-peritoneal space may be facilitated with the pocket. The prosthesis may provide a surgeon the benefit of laparoscopic mesh placement through an open repair, eliminating the need for costly equipment or general anesthesia. The contemplated technique does not require dissection or fixation in the subaponeurotic plane. It is to be understood that the prosthesis may have other applications and be used with for other repair procedures as should be apparent to one of skill in the art.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An implantable prosthesis for repairing a tissue or muscle wall defect, the implantable prosthesis comprising:
   a patch of repair fabric including a body portion that is constructed and arranged to cover the tissue or muscle wall defect, the body portion including a first side to face toward the tissue or muscle wall defect and a second side to face away from the tissue or muscle wall defect; and
   no more than two pockets to facilitate deployment and/or placement of the prosthesis at the tissue or muscle wall defect, the pockets including a single pocket located on the first side of the body portion and a single pocket located on the second side of the body portion opposite the first side, the pockets located directly opposite each other at a first end portion of the patch.

2. The implantable prosthesis according to claim 1, wherein the patch includes at least first, second and third layers of fabric attached together to create the pockets therebetween.

3. The implantable prosthesis according to claim 2, wherein the second layer of fabric is positioned over at least a portion of a first side of the first layer of fabric and the third layer of fabric is positioned over at least a portion of a second side of the first layer of fabric, the pocket located on the first side of the body portion being located between the first and second layers and the pocket located on the second side of the body portion being located between the first and third layers.

4. The implantable prosthesis according to claim 3, wherein the second layer includes an edge extending across the portion of the first surface of the first layer and the third layer includes an edge extending across the portion of the second surface of the first layer.

5. The implantable prosthesis according to claim 4, wherein the patch includes a first opening to provide access to the pocket located on the first side of the body portion and a second opening to provide access to the pocket located on the second side of the body portion.

6. The implantable prosthesis according to claim 5, wherein the first opening is located along the edge of the second layer and the second opening is located along the edge of the third layer.

7. The implantable prosthesis according to claim 1, further comprising a member to help deploy and/or hold the body portion in a spread out configuration.

8. The implantable prosthesis according to claim 7, wherein the member surrounds the body portion of the patch.

9. The implantable prosthesis according to claim 8, wherein the member includes an indentation that is adapted to be positioned adjacent a body structure, the indentation formed by a portion of the member deviating inwardly toward the body portion.

10. The implantable prosthesis according to claim 9, wherein the indentation has a curved shape.

11. The implantable prosthesis according to claim 10, wherein the member has a convex shape along a substantial portion thereof and the indentation has a concave shape.

12. The implantable prosthesis according to claim 9, wherein the patch has an oval shape with a major axis and a minor axis, the patch including an obtuse end portion and an acute end portion, the obtuse end portion being larger than the acute end portion.

13. The implantable prosthesis according to claim 12, wherein the pockets are located at the obtuse end portion.

14. The implantable prosthesis according to claim 13, wherein the indentation is offset from the minor axis toward the acute end portion.

15. The implantable prosthesis according to claim 7, wherein the member has a resiliency that allows the member to deform from an initial shape and then return to the initial shape to return the body portion of the patch to the spread out configuration.

16. The implantable prosthesis according to claim 1, wherein the repair fabric is susceptible to the formation of adhesions with tissue and organs.

17. The implantable prosthesis according to claim 1, wherein the repair fabric has a plurality of interstices that are constructed and arranged to allow tissue ingrowth.

* * * * *